United States Patent [19]

Müller et al.

[11] 4,160,113

[45] Jul. 3, 1979

[54] PROCESS FOR THE MANUFACTURE OF RESORCINOL

[75] Inventors: Werner H. Müller, Kelkheim; Knut Riedel, Hofheim; Hans Krekeler, Wiesbaden, all of Fed. Rep. of Germany

[73] Assignee: Hoechst Aktiengesellschaft, Frankfurt am Main, Fed. Rep. of Germany

[21] Appl. No.: 850,815

[22] Filed: Nov. 11, 1977

Related U.S. Application Data

[63] Continuation of Ser. No. 602,028, Aug. 5, 1975, abandoned.

[30] Foreign Application Priority Data

Aug. 7, 1974 [DE] Fed. Rep. of Germany ....... 2437983

[51] Int. Cl.$^2$ .............................................. C07C 39/08

[52] U.S. Cl. .................................. 568/772; 568/740; 568/744; 568/766

[58] Field of Search ...................... 260/621 H, 621 D; 568/772, 744, 740, 766

[56] References Cited

U.S. PATENT DOCUMENTS 3,865,884   2/1975   Agusto et al. .................. 260/621 H

*Primary Examiner*—Werren B. Lone
*Attorney, Agent, or Firm*—Curtis, Morris & Safford

[57] ABSTRACT

The present invention is related to a process for the manufacture of resorcinols by catalytic dehydrogenation of cyclohexane diones-(1,3) in the liquid phase by means of a dehydrogenating mixture consisting of a solvent and of a catalyst containing a noble metal from Group VIII of the Periodic Table.

7 Claims, No Drawings

PROCESS FOR THE MANUFACTURE OF RESORCINOL

This is a continuation application of prior application Ser. No. 602,028, filed on Aug. 5, 1975, now abandoned.

Resorcinol is essentially used as synthetic resin component of resorcinol-aldehyde-resins for the rubber and wood glue industries. Substituted resorcinols are employed as coupling components of dyestuffs, e.g. for diazo printing. The manufacture on a technical scale is carried out, for example, by having benzene react with $SO_3$, subsequent alkali fusion of the neutralized benzene disulfonic acid with caustic soda and by acidification of the thus produced resorcinol disodium salt with sulfuric acid. This process has the drawback that large quantities of salt ($Na_2SO_4$) are formed at rates which surpass by several times the quantities of resorcinol which are produced by the same process so that the waste waters are subject to considerable contamination.

It is also known that resorcinol may be produced by dehydrogenation of cyclohexane-dione in the presence of a palladium catalyst. This method being described by British Pat. No. 1 188 387, is handicapped by small yields in resorcinol of only 26%, calculated on the quantity of cyclohexane-dione-(1,3) charged.

Cyclohexane-diones-(1,3) are accessible meanwhile according to German Offenlegungsschrift No. 2 245 270 by cyclization of 4-oxocarboxylic acid esters at excellent yield rates.

A process for the manufacture of resorcinols, having the formula

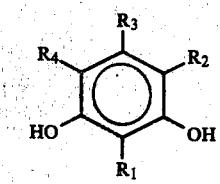

has now been found wherein the radicals $R_1$ to $R_4$ may be identical or different and represent hydrogen, straight-chain, branched or cyclic alkyl groups which may as well carry substituents, or aryl groups which may also carry substituents, which comprises that cyclohexane diones-(1,3) of formula

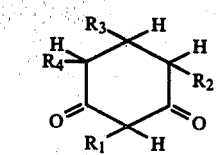

wherein $R_1$ to $R_4$ have the above mentioned meaning are added to a dehydrogenation mixture composed of a solvent and of a catalyst containing a noble metal of the eighth subgroup of the periodical system under a pressure of from 0.5 to 20 atmospheres and at a temperature of from 160° to 350° C. in such a way that the concentration in cyclohexane-dione which is to be dehydrogenated does not surpass 30%, calculated on the weight of the liquid phase.

Especially suitable straight-chain, branched or cyclic alkyl groups are those having up to 12 carbon atoms such as for example methyl, ethyl, propyl, butyl, pentyl, hexyl, octyl, decyl, dodecyl, cyclopentyl, cyclohexyl, cyclododecyl. Alkyl groups with a double bond are also suitable, e.g. the allyl group.

The alkyl radicals may furthermore be substituted for example by halogens, especially fluorine and chlorine, or by a phenyl, naphthyl, amino, hydroxy, keto, carboxy, carbamide or nitrile group, but as well by a carbalkoxy group having up to 6 carbon atoms such as carboxymethyl (—COOCH$_3$) or by carboxyethyl (—COOC$_2$H$_5$).

Suitable aryl groups are for example those having from 6 to 14 carbon atoms, preference is given to the phenyl radical and to the naphthyl radical. The aryl groups may also carry substituents, e.g. halogen, especially fluorine and chlorine, alkyl groups having up to 6 carbon atoms, or by trifluoromethyl groups, pentafluoro-ethyl or nitro groups. There may also be considered for example alkoxy groups having up to 6 carbon atoms, such as the methoxy or ethoxy group.

Especially suitable noble metals are palladium, platinum, ruthenium and rhodium. These catalysts are generally employed on carrier materials such as carbon, aluminum oxide, silicic acid, magnesium oxide, calcium oxide, titanium oxide and asbestos, preference is given to the use of palladium on carbon. The useful concentration rate of the noble metal varies from 0.02 to 20%, calculated on the weight of the carrier material, preferably from 0.1 to 10 weight %.

The process may be carried through continuously or discontinuously, at temperatures from 160° to 350° C., preferably from 180° to 260° C., since the latter temperatures achieve a particularly high selectivity combined with a very rapid dehydrogenation.

The reaction pressure varies from 0.5 to 20 atmospheres, being preferably chosen at such a level that it is sufficient for maintaining a liquid phase.

Preference is given to keeping low the partial pressure of the hydrogen which is formed during the dehydrogenation so as to shift the equilibrium in favor of the dehydrogenation and to avoid a hydrogenation or hydrogenolysis of the starting compounds and the final products. This low partial pressure of hydrogen may be achieved by purging the reaction system with an inert gas, such as nitrogen or carbon dioxide.

Suitable solvents are aliphatic ethers, aliphatic esters such as e.g. succinic acid dialkyl ester or propane-diol-diacetate or butane-diol-diacetate, aromatic ethers such as diphenyl ether; hydrocarbons such as benzene, toluene, xylene, pseudocumene, naphthalene, biphenyl, tetralene, decalene; ketones such as acetone, diethylketone, methyl-ethylketone or methylisobutyl ketone. Also suitable are acid amides such as dimethyl formamide or N-methyl-pyrrolidone, alcohols, phenols and water. Preferred solvents are aliphatic ethers such as the polyglycol dialkyl ethers, e.g. diethylene glycol dialkyl ether, triethylene glycol dialkyl ether or tetraethylene glycol dialkyl ether having generally alkyl groups with up to 6 carbon atoms.

Special preference is given to the polyglycol dimethyl ethers and polyglycol diethyl ethers. The polyglycol dialkyl ethers have the advantage that they boil under an atmospheric pressure in the preferred temperature range from 180° to 260° C.—a fact which has a particularly favorable effect on the process, since it allows for operating under normal pressure and since the dehydrogenation is carried out with special speed and selectivity under reflux conditions within the preferred temperature range. The efficiency of the process is enhanced by vigorous agitation of the reaction mixture as long as it is contacting the catalyst.

When the reaction is carried out discontinuously, an especially convenient embodiment is the addition under reflux conditions of the cyclohexane dione which is dehydrogenated dissolved in an easily volatile solvent such as acetone, isopropanol, methanol or water to the dehydrogenation mixture consisting of a catalyst suspension and polyglycol ether as solvent. The solvent for the cyclohexane dione is thereby removed from the reaction mixture by distillation via a descending condenser. The hydrogen which is thereby produced contributes additionally to improve the thorough mixing. After completion of the reaction the reaction mixture is filtered off the catalyst and the resorcinal thus produced is obtained in its pure state by distillation of the filtrate.

When the reaction is carried out continuously, a solution of a cyclohexane dione in the same solvent which is also employed for the suspension of the catalyst, is introduced continuously via a preheating device into the dehydrogenation reactor, while simultaneously a corresponding quantity of the reaction mixture containing the resorcinol produced is discharged. In that case the catalyst is either retained in the reactor by means of a frit, or, after separation e.g. by means of a hydrocyclone, fed back into the reactor. After having separated by distillation the resorcinol produced from the solvent, the latter is re-used for dissolving newly introduced cyclohexane-dione for dehydrogenation.

The process according to the invention can be carried out with a fixed-bed catalyst or with a catalyst which is maintained in suspension by stirring the reaction solution vigourously.

When using a fixed-bed catalyst, a dimension of from 0.5 to 10 mm, preferably from 2 to 5 mm is recommended for the catalyst particles. Larger particles reduce the efficiency of the catalyst, while smaller particles may lead to losses in catalyst and to blocking of the catalyst bed.

When the process is carried out with a supported catalyst and suspended in the reaction medium, the size of the catalyst particles varies generally from 0.01 to 5 mm, preferably from 0.05 to 1 mm. The smaller particles represent the drawback of hardly separating from the reaction solution. The disadvantage of larger particles is the difficulty to maintain them in suspension and the minor dehydrogenation speed. Depending on the type of the liquid and of the catalyst, the suspension may contain from 0.1 to 40 parts by weight of catalyst on a carrier material—in relation to 100 parts by weight of the liquid. Preferred proportions are from 1 to 30 parts by weight of supported catalyst per 100 parts by weight of solvent.

The process according to the invention has the advantage that dehydrogenation takes places immediately upon introduction of the cyclohexane dione into the dehydrogenation mixture, so that the rather unstable cyclohexane-dione-(1,3) is converted immediately to the resorcinol being very stable under the dehydrogenation conditions.

The process according to the invention achieves much higher yields in resorcinol by catalytic dehydrogenation of cyclohexane-diones-(1,3) than those obtained according to known processes.

The following examples illustrate the invention:

EXAMPLES 1–8 (cf. table)

A mixture of 50 ml of solvent and 1 g of dehydrogenation catalyst is heated to 180°–220° C. while agitating and purging with nitrogen, in a 100 ml three-necked flask, equipped with thermometer, agitator, dropping funnel and descending condenser (Claisen-bridge). Subsequently, the cyclohexane-dione in a solvent which is either identical with the solvent used for the catalyst suspension or which boils considerably lower is added in such a way that the cyclohexane-dione concentration does not surpass 30 weight %, calculated on the weight of the liquid phase. The operation is controlled by a gas meter measuring the quantity of hydrogen which is formed during the reaction. During the addition, the temperature is maintained within the range of from 180° to 230° C. After having completed the addition of cyclohexane-dione, the temperature is kept at 220°–230° C. for a short while until no more hydrogen is produced. Cooling takes then place while purging with nitrogen, the catalyst is separated and the filtrate is analyzed by GLC and finally subject to distillation in vacuo. After fractionating the solvent (e.g. in the case of diethylene glycol diethyl ether the boiling point is 78°–84° C. under 15 mm/Hg) the desired resorcinol is obtained in its pure state (boiling point 158° C. under 15 mm/Hg). The solvent may be recycled.

If methanol is used as solvent (example 5), which esterifies with cyclohexane-dione to yield 3-methoxy-cyclo-hexanone, resorcinol-monomethyl ether is formed as by-product.

TABLE

Dehydrogenation of cyclohexanedione-(1,3) = CD, m.p. 104° C.
Catalyst: 0.1 g Pd on 0.9 g of active carbon

| Example | reaction medium (50 ml) | solvent for CD (type, ml) | g | temp. (°C.) | time (min.) | $H_2$ (ml) | yields (resorcinol) | (mole % phenol) |
|---|---|---|---|---|---|---|---|---|
| 1 | PEG | IPOH, 45 | 6 | 213 | 50 | 1400 | 94 | 4,2 |
| 2 | " | IPOH, 50 | 12 | 212 | 102 | 2230 | 82 | 5,2 |
| 3 | " | acetone, 60 | 6 | 210 | 80 | 1340 | 82 | 5,0 |
| 4 | " | $H_2O$, 30 | 6 | 208 | 64 | 1360 | 84.1 | 3,4 |
| 5 | " | MeOH, 30 | 6 | 212 | 40 | 1240 | 47.1 | 3,8* |
| 6 | DEG | DEG, 50 | 6 | 195 | 60 | 1460 | 86.3 | — |
| 7 | NMP | IPOH, 50 | 6 | 187 | 50 | 990 | 64.2 | — |
| 8 | BP | IPOH, 45 | 6 | 213 | 50 | 880 | 55.0 | — |

*28 mole % resorcinol monomethyl ether
DEG = diethylene glycol diethyl ether
NMP = N-methyl pyrrolidone
BP = biphenyl
PEG = polyglycol ether (90% tri-, 10% tetraethylene glycol diethylether)

EXAMPLE 9

A mixture of 100 ml of diethylene glycol diethyl ether and 1 g of catalyst (0.1 g Pd on 0.9 g of powdery carbon <0.05 mm) is heated to 190° C. while purging with nitrogen, in a 250 ml three-necked flask, equipped with agitator, thermometer and descending cooling device. Subsequently, a solution of 22 g of 2,6-dimethyl-3-hydroxycyclohexene-(2)-one (prepared from 4-methyl-5-oxo-heptanoic-acid methyl ester according to German Offenlegungsschrift No. 2 245 270) in 210 ml of isopropanol is added within two hours, the temperature being maintained at 185° C. The isopropanol is removed continuously by distillation. The development of hydrogen stopped after completion of the addition of the cyclohexane-dione. The contents of the reactor were cooled, the catalyst was filtered off and the filtrate distilled in vacuo. After the diethylene glycol diethyl ether (boiling point 72° C. under 14 mm/Hg) 18.5 g (=85.3% of theoretical yield) of 2,6-dimethyl resorcinol are passing over at the boiling point of 112° C. under 2 mm/Hg which cristallize in the collector recipient (m.p. 107° C. from benzene).

What is claimed is:

1. A process for making a resorcinol having the formula

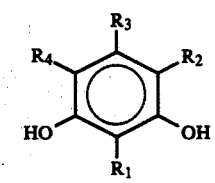

wherein $R_1$ to $R_4$ are members selected from the group consisting of H, straight-chain, branched chain, cyclic alkyl, each having up to 12 carbon atoms, phenyl and naphthyl, which comprises catalytically dehydrogenating in liquid phase a cyclohexane dione-(1,3) of the formula

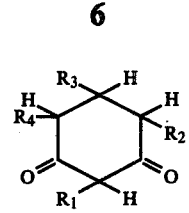

wherein $R_1$ to $R_4$ have the above-mentioned meaning;

by adding said cyclohexane dione-(1,3) to a solvent mixture consisting essentially of a solvent selected from the group consisting of diethylene glycol dialkyl ether, triethylene glycol dialkyl ether and tetraethylene glycol dialkyl ether, wherein said alkyl contains up to 6 carbon atoms and a catalyst selected from the group consisting of palladium, platinum, ruthenium and rhodium;

catalytically dehydrogenating said cyclohexane dione-(1,3) at about atmospheric pressure and a temperature of from 180° to 260° C., controlling the concentration of said cyclohexanone dione-(1,3) at no more than 30% by weight, based on weight of the liquid phase; and separating and recovering said resorcinol.

2. The process of claim 1 wherein the catalyst is supported on a carrier and the catalyst comprises 0.1 to 40 parts by weight per 100 parts by weight of solvent.

3. The process of claim 2 wherein the catalyst comprises 1 to 30 parts by weight per 100 parts by weight of solvent.

4. The process according to claim 1 wherein the reaction is carried out at a temperature in the range of from 180° to 260° C.

5. The process of claim 1 wherein cyclohexane dione-(1,3) is added to a solvent mixture consisting essentially of a solvent selected from the group consisting of diethylene glycol diethyl ether, triethylene glycol diethylether and tetraethylene glycol diethylether and said noble metal is palladium.

6. The process of claim 1 wherein said catalyst is supported on a carrier which is a member selected from the group consisting of carbon, aluminum oxide, silicic acid, magnesium oxide, calcium oxide, titanium oxide and asbestos.

7. The process of claim 1 wherein said catalyst comprises palladium supported on a carbon carrier and the palladium consists of 0.02 to 20% by weight of the catalyst.

* * * * *